United States Patent [19]
Dalton et al.

[11] Patent Number: 5,801,247
[45] Date of Patent: Sep. 1, 1998

[54] PROCESS FOR THE ENANTIOSELECTIVE SYNTHESIS OF HYDROXYPYRROLIDINES FROM AMINO ACIDS AND PRODUCTS THEREOF

[75] Inventors: David R. Dalton, Radnor; Yifang Huang, Cheltenham, both of Pa.

[73] Assignee: Temple University-of the Commonwealth System of Higher Education, Philadelphia, Pa.

[21] Appl. No.: 787,994

[22] Filed: Jan. 23, 1997

[51] Int. Cl.$^6$ .................... C07D 207/12; C07D 263/14
[52] U.S. Cl. .................... 548/201; 548/237; 548/239; 548/544
[58] Field of Search .................... 548/201, 237, 548/239, 544

[56] References Cited

U.S. PATENT DOCUMENTS

| | | | |
|---|---|---|---|
| 2,446,192 | 8/1948 | Pfister, III et al. | 548/239 X |
| 2,530,627 | 11/1950 | Pfister, III et al. | 548/239 X |
| 2,571,940 | 10/1951 | Pfister, III et al. | 548/239 |
| 2,772,281 | 11/1956 | Holly et al. | 548/239 |
| 2,846,439 | 8/1958 | Joyama et al. | 548/239 |
| 3,310,571 | 3/1967 | Lambert | 548/239 X |
| 4,702,864 | 10/1987 | Magolda et al. | 548/239 X |
| 4,978,759 | 12/1990 | Jouin et al. | 548/497 |
| 5,104,984 | 4/1992 | Salzmann et al. | 540/200 |
| 5,229,523 | 7/1993 | Wong et al. | 548/544 |
| 5,250,704 | 10/1993 | Van Le et al. | 548/557 |
| 5,276,120 | 1/1994 | Wong et al. | 546/184 |
| 5,290,948 | 3/1994 | Reitz et al. | 548/541 |
| 5,300,660 | 4/1994 | Federsel et al. | 548/566 |
| 5,352,591 | 10/1994 | Wong et al. | 548/541 X |
| 5,461,143 | 10/1995 | Wong et al. | 536/17.5 |
| 5,466,809 | 11/1995 | Dime | 546/183 |
| 5,468,876 | 11/1995 | Federsel et al. | 548/535 |
| 5,525,735 | 6/1996 | Gallop et al. | 548/533 |

OTHER PUBLICATIONS

Provencher, L., et al., "Five–Membered ring Azasugars as Potent Inhibitors of α–L–Rhamnosidase (Naringinase) from *Penicillium decumbens*", Bioorgan. & Medic. Chem., 2(11):1179–1188 1994.
Furukawa, J., et al., "3,4–Dihydroxy–2–Hydroxymethylpyrrolidine from *Arachniodes Standishii* ", Phytochemistry, 24(7):593–594, 1985.
Robinson, K.M., et al., "Intestinal disaccharidase inhibitors", Drugs of the Future, 17(8):705–720, 1992.
Nash, R.J., et al., "2–Hydroxymethyl–3,4–Dihydroxypyrrolidine in Fruits of *Angylocalyx Boutiqueanus* " Phytochemistry, 24(7):1620–1622, 1985.
Pearson, W.H., et al., "A Practical Synthesis of (–)–Swainsonine", J. Org. Chem., 61:7217–7221, 1996.
Fronza, G., et al., "On the Use of (4S, 5S)–2–Phenyl–4, 5–Dimethyl–4–Formyl–4,5–Dihydro–Oxazole in Synthesis of N–Protected 2,3,4, 6–Tetradeoxy–4–C–Methyl–4–Amino–L–Hexose Derivatives", J. Carbohydrate Chem., 10(2):197–213, 1991.
Chikashita et al., Chemical Abstracts, 114:23841 (1991).
Eggleton et al., Chemical Abstracts, 101:54975u (1984).
Elliott, J. Chem. Soc., 589 (1949).
Elliott, J. Chem. Soc., 62 (1950).
Corey et al., Tetrahedron Lett., 34(44), 6969–6972, 1993.
Huang et al., J. Org. Chem., 62, 372–376, 1997.
Lafargue et al., Synlett, 1995, 171–172.
Meyers et al., Synthesis, 1993, 2, 250–82.
Morell et al., J. Org. Chem., 42(2), 355–356, 1977.
Mori et al., Tetrahedron, 41(12), 2379–2386, 1985.
Pfister, 3rd, et al, J. Am. Chem. Soc., 71, 1101–1105, 1949.
Seebach et al., Tetrahedron Lett., 24(32), 3311–3314, 1983.
Tkaczuk et al., J. Org. Chem., 46, 4393–4398, 1981.
Wipf et al., Tetrahedron Lett., 33(7), 907–910, 1992.

*Primary Examiner*—Fiona T. Powers
*Attorney, Agent, or Firm*—Ratner & Prestia

[57] ABSTRACT

The present invention relates to processes for the enantioselective synthesis of hydroxypyrrolidines from amino acids. An amino methyl ester is used as the starting material. The ester is reacted with a benziminoethyl ether to produce an oxazoline or thiazoline. Specifically, L-serine methyl ester is used to produce 4-(carbomethoxy)-2-phenyl-$\Delta^2$-oxazoline, and cysteine is used to produce the corresponding thiazoline. The oxazoline (or thiazoline) can be reduced to an aldehyde by treatment with a slight excess of DIBAL-H. The oxazoline is quenched with alcohol and reacted with (carbomethoxymethylene)triphenylphosphorane, to produce (S)-(+)-methyl (E)- and (S)-(–)-methyl (Z)-3-(4,5-dihydro-2-phenyl-4-oxazolyl)-2-propenoate. The double bond is hydroxylated to yield the diol esters. The resulting diol is then treated with aqueous acid to hydrolyze the oxazoline and recyclize to produce 3,4-dihydroxy-5-hydroxymethylpyrrolidone benzoate. This is treated with an excess of borane in tetrahydrofuran to yield (2-hydroxymethyl) 3,4-dihydroxypyrrolidine. The intermediate compounds are useful both in the present process and as final products themselves. The total yield of the mixture of isomers, as well as their ratio, can be varied.

12 Claims, No Drawings

PROCESS FOR THE ENANTIOSELECTIVE SYNTHESIS OF HYDROXYPYRROLIDINES FROM AMINO ACIDS AND PRODUCTS THEREOF

BACKGROUND OF THE INVENTION

1. Field of the Invention

The present invention relates to azasugar compounds, and more particularly to the efficient synthesis thereof.

2. Description of Related Art

Carbohydrates are a large class of natural substances that structurally are polyhydroxycarbonyl compounds and their derivatives. Carbohydrates generally correspond to the formula $(C)_n(H_2O)_n$ where n is an integer usually greater than 3.

Monosaccharides are simple carbohydrates that cannot be further hydrolyzed into simpler types of carbohydrates. A monosaccharide having a six-membered ring is referred to as a pyranose, whereas a five-membered ring monosaccharide is referred to as furanose. A pyranose or furanose lacking one or more hydroxyl groups normally present in a carbohydrate is referred to as a deoxypyranose or deoxyfuranose, with the carbon chain position at which the hydroxy is absent being indicated.

Azasugars are a class of saccharides in which the ring oxygen is replaced by an imino group (—NH—). A six-membered ring azasugar can be referred to as an azapyranose or a polyhydroxylated piperidine compound. A five-membered ring azasugar can be referred to as an azafuranose or a polyhydroxylated pyrrolidine. An azasugar can also be named as an aza derivative of an otherwise systematically or trivially named pyranose or furanose monosaccharide.

One group of azasugars which are derived from piperidines (azapyranoses), can be hyrdroxylated at the 3-,4- and 5-positions, have hydrogen at the 6-position and can have a methyl group or hydrogen at the 2-position, the 1-position being the nitrogen atom, in piperidine nomenclature. Dideoxyazapyranoses are the polyhydroxylated piperidines as discussed above, that have either a methyl group or hydrogen at the 5-position, hydrogen at the 1-position and can have hydroxyl groups elsewhere on the ring, as above, in pyranose nomenclature. Pyranose nomenclature and numbering will usually be used herein for six-membered ring compounds, unless otherwise specified.

Another group of azasugars described herein are derived from pyrrolidines (azafuranoses). These compounds can be hydroxylated at the 3- and 4-positions, have a hydroxymethyl group at the 5-position, and a methyl or hydroxymethyl at the 2-position, the 1-position being the nitrogen atom, in pyrrolidine nomenclature. A 2-hydroxymethyl group in pyrrolidine nomenclature corresponds to a 2-hydroxymethyl or 4-hydroxymethyl group in furanose nomenclature. Dihydroxyazafuranoses are the polyhydroxypyrrolidines discussed above that have an hydroxymethyl at the 4-position and a hydrogen at the 2-position or a hydrogen at the 4-position and an hydroxymethyl at the 2-position, and can have hydroxyl groups at the other positions, using furanose numbering. Pyrrolidine nomenclature and numbering will usually be used herein for these azasugars, unless otherwise specified.

It is now clear that these carbohydrates mediate the related properties of cell-cell recognition (necessary for cellular aggregation and differentiation) and cell-cell fusion (necessary for the subsequent transmission of information). Glycosidases, intimately involved in those and related processes, have been shown to be inhibited by some of the members of the group of eight stereoisomeric 2-hydroxymethyl-3,4-dihydroxy-pyrrolidines, and related nitrogenous materials. It has even been suggested that these and other aminosugars could bind directly to viral or host-cell carbohydrate receptors to produce the results of their biological activity. As such, azasugars can be useful for treating metabolic disorders such as diabetes, as antiviral agents, as antimicrobial agents, or as anticancer agents. Exploration of their mode(s) of action has only begun.

Despite their clear usefulness, there is still a need for an effective synthesis of novel azasugars and their derivatives. Both carbohydrate and noncarbohydrate precursors have been employed in syntheses of the members of the pairs of enantiomers of imino -ribitol, -arabinitol, -xylitol, and -lyxitol. In general, the routes are complex and it is possible that this may have impeded exploration of their full potential.

SUMMARY OF THE INVENTION

The present invention relates to processes for the enantioselective synthesis of azasugars from amino acids. An amino methyl ester is used as the starting material. The ester is reacted with a benziminoethyl ether to produce an oxazoline or thiazoline. Specifically, L-serine methyl ester can be used to produce 4-(carbomethoxy)-2-phenyl-$\Delta^2$-oxazoline, or cysteine can be used to produce the corresponding thiazoline. The oxazoline can be reduced to the aldehyde by treatment with a slight excess of DIBAL-H (diisobutylaluminum hydride). This is quenched with alcohol and reacted with (carbomethoxymethylene) triphenylphosphorane, to produce (S)-(+)-methyl (E)- and (S)-(–)- methyl (Z)-3-(4,5dihydro-2-phenyl-4-oxazolyl)-2-propenoate. The double bond is hydroxylated to yield the diol esters. The resulting diol is then treated with aqueous acid, whereby hydrolysis of the oxazoline and recyclization takes place resulting in the formation of 3,4-dihydroxy-5-hydroxymethylpyrrolidone benzoate. This is treated with an excess of borane in tetrahydrofuran to give the resulting (2-hydroxymethyl) 3,4-dihydroxypyrrolidine. The intermediate compounds are useful both in the present process and as final products themselves. The total yield of the mixture of isomers, as well as their ratio, can be varied.

DETAILED DESCRIPTION OF THE PREFERRED EMBODIMENTS

As shown by reaction Scheme I, the starting material for the present synthesis has the general form of compound 2. The groups containing $X_1$ and $X_2$ can be in either position around the chiral center. Note that if $X_2$=H, no chiral center is present. Commonly, threonine methyl ester ($X_1$=O, $X_2$=CH$_3$), serine methyl ester ($X_1$=O, $X_2$=H), and cysteine methyl ester ($X_1$=S, $X_2$=H) are used. Other $C_1$-$C_4$ esters may also be used. (e.g. serine ethyl ester). The following will describe the specific reactions which occur when L-serine methyl ester is used.

L-serine methyl ester 2 can be reacted with benziminoethyl ether (2a, $R_1$, $R_2$, $R_3$=H) to form the known, readily available 4-(carbomethoxy)-2-phenyl-$\Delta^2$-oxazoline 3. The benziminoethyl ether 2a may be substituted on the benzene ring by any of various substituents. These substitutions will not affect the resulting azasugar, the substitutions will affect the intermediate products and their usefulness. Generally, electron-donating hydrophobic groups may be substituted for $R_{1-3}$. Specifically, $R_1$, $R_2$, and $R_3$ are preferably selected from the group consisting of H, $C_1$-$C_4$ alkanes, and $C_1$-$C_4$ ethers.

Although the present invention will be described for L-isomer, results for the D-serine isomer are the same. Only the L-serine isomer has been shown here, but is should be understood that the D-serine can be substituted to yield the appropriate stereoisomer products.

temperature, reduction to the aldehyde occurs. As the aldehyde is labile, an alcohol quench of the reaction mixture is followed, in the same flask, by direct addition of carboalkoxymethylene triphenylphosphorane, as shown in Scheme II.

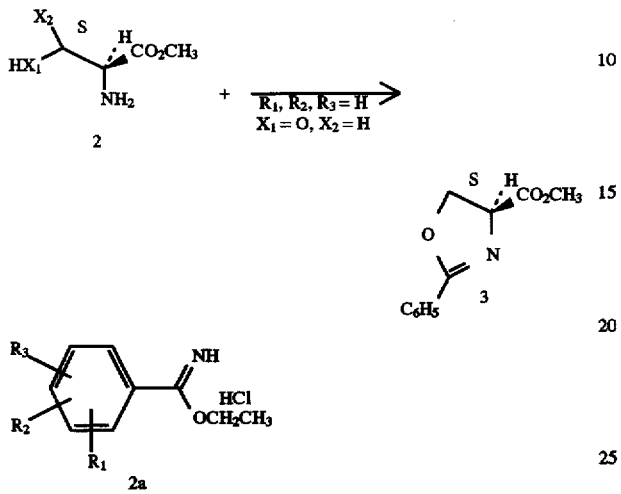

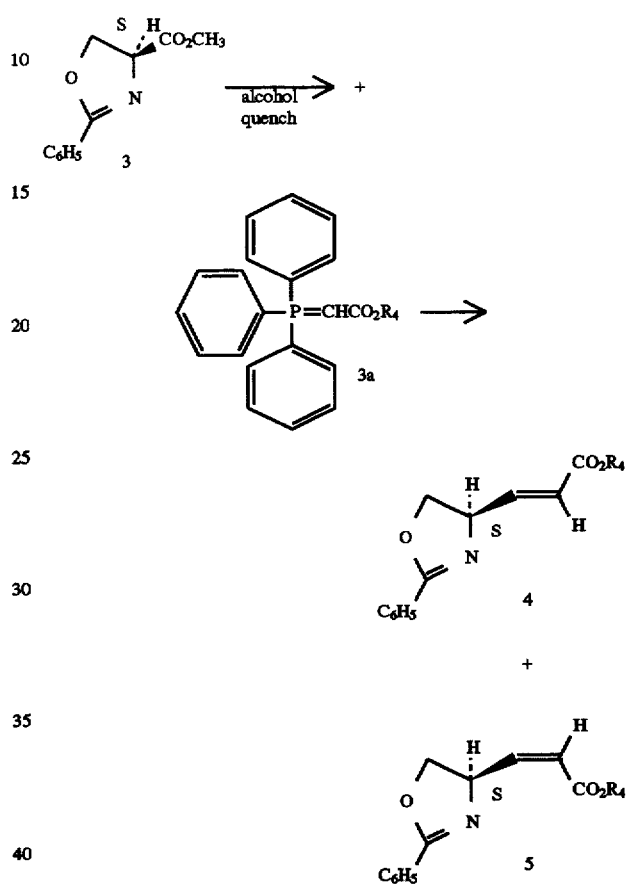

It should be noted that, where applicable throughout these descriptions, satisfactory elementary analysis (Galbraith Laboratories, Knoxville, Tenn.) and/or high resolution mass spectrometric analysis (The Pennsylvania State University, University Park, Pa. or Drexel University, Philadelphia, Pa.) have been obtained for all new compounds. $^1$H (300 MHz) and $^{13}$C (75 MHz) NMR spectra were obtained on a GE QE-300 NMR spectrometer. Chemical shifts are reported in parts per million (PM), δ, from TMS=0.00 ppm. Infrared (FT-IR) spectra were taken as neat oils (for noncyrstalline materials) or as KBr pellets for crystalline samples on Mattson 4020, Nicolet 800, or Digilab FTS-40 spectrometers. Solvents, reactive reagents, and column materials were purchased from Acros Chemical, Fisher Scientific, and/or Aldrich Chemical Companies. Solvents were distilled under argon prior to use. L- and D-serine were obtained from Acros Chemical Co., through Fisher Scientific, Pittsburgh, Pa. Optical rotations were taken as noted in a Perkin-Elmer 341 Polarimeter.

L-serine methyl ester hydrochloride (25 g, 161 mmol) was then suspended in dry methylene chloride (350 ml) and triethyl amine (28 ml, 20.3 g, 200 mmol) added. When the dissolution of the amine hydrochloride was complete, benziminoethyl ether hydrochloride (29.8 g, 162 mmol) was added as one portion. The reaction mixture was heated at reflux on the steam bath for 4 h and then stirred at room temperature, under argon, overnight. The pink reaction mixture was extracted twice with saturated sodium bicarbonate and the combined aqueous extracts back washed twice with half its volume of methylene chloride. The combined methylene chloride extracts were washed with brine, dried over magnesium sulfate, filtered, and the solvent removed at reduced pressure. Flash chromatography on silica gel (eluted with 1:1 ether:petroleum ether) provided the oxazoline methyl ester in 80% yield (26.4 g, 128.8 mmol), $[\alpha]^{20}{}_D$=+117.2°, c=0.053 in CHCl$_3$). $^1$H NMR ($^2$HCCl$_3$) Δ7.98–8.01 (m, 2H); 7.48–7.54 (m, 1H); 7.39–7.45 (m, 2H); 4.97 (dd, J=7.8, 10.5, 1H); 4.71 (dd, J=8.7, 8.1, 1H); 4.60 (dd, J=10.5, 8.7, 1H); 3.83 (s, 3H).

When the resulting 4-(carbomethoxy)-2-phenyl-Δ$^2$-oxazoline 3 is treated with a slight excess of Dibal-H at low In this reaction, R$_4$ is selected from the group consisting of C$_1$–C$_4$ alkanes. Selection of R$_4$ should be made carefully as it will likely affect the ratio of cis and trans isomers formed. Where R$_4$=CH$_3$, 3a is carbomethoxymethylene triphenylphosphorane, and Scheme II becomes Scheme IIa:

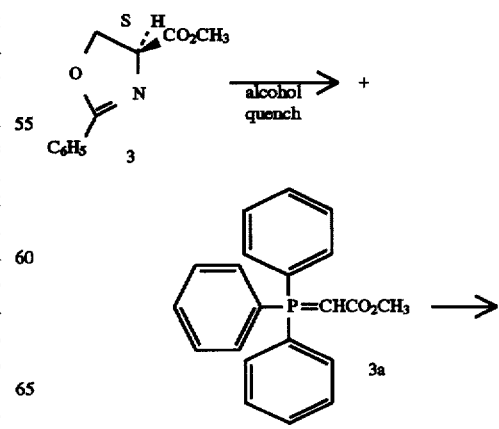

-continued
Scheme IIa

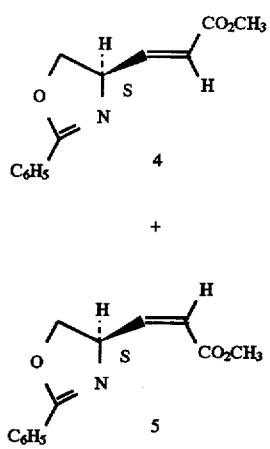

This results in the formation of a mixture of S-(+)-methyl (E)-3-(4,5-dihydro-2-phenyl-4-oxazolyl)-2-propenoate, 4, ($[\alpha]^{20}_D$=+60.2°, c=0.018 in $CHCl_3$), and the corresponding S-(−)-methyl (Z)-isomer 5, ($[\alpha]^{20}_D$=−49.5°, c=0.094 in $CHCl_3$).

Experimentally, the oxazoline methyl ester 3 (26.5 g, 129 mmol) in dry toluene (800 ml) was cooled to −78° C. under an argon atmosphere and DIBAL-H (1.5M, 137 ml) was added slowly, keeping the temperature of the toluene solution below −70° C. throughout. After stirring at −78° C. for an additional 3 hours, methanol (100 ml) was added, again keeping the temperature below −70° C., to terminate the reaction and, 30 min later, carbomethoxymethylene triphenylphosphorane (48.5 g, 150 mmol) in methanol (300 ml) was added and the reaction solution allowed to warm to room temperature. After stirring overnight, the solution was diluted with diethyl ether (600 ml) and extracted (2×150 ml) with aqueous sodium hydroxide (15%), twice (2×150 ml) with saturated sodium bicarbonate, and twice (2×150 ml) with brine. The solvent mixture was removed at reduced pressure and the residue suspended in light petroleum ether (300 ml). The crystalline triphenylphosphine oxide was removed by filtration and the residue, after removal of the solvent, chromatographed on silica gel, eluting with 80:20 ether:petroleum ether. The mixture (72% of theory) was 64% 5 (19.0 g) and 8.4% 4 (2.5 g).

The isomeric alkenes were easily separated by column chromatography.

Interestingly, the total yield of the mixture of isomers, and their ratio can be varied by altering the conditions of the alcohol quench and the subsequent Wittig reaction. For example, if the reaction mixture is quenched with t-butanol before carbomethoxymethylene triphenylphosphorane is added, 4 and 5 are produced in an overall yield of 83% and in a 1.5:1 ratio, respectively. Alternatively, quenching the reaction with methanol but holding everything else the same, provides a 72% yield of the mixture of 4 and 5 but now in a 1:8.5 ratio.

For the E isomer, 4, colorless oil, $R_f$ 0.17, silica gel, 20:80 diethyl ether :petroleum ether, $[\alpha]^{20}_D$=+60.2°, c=0.018 in $CHCl_3$. $^1H$ ($^2HCCl_3$) Δ7.96–8.00 (m, 2H); 7.49–7.54 (m, 1H); 7.40–7.46 (m, 2H); 7.00 (dd, J=6.3, 15.6, 1H); 6.11 (dd, J=1.5, 15.6, 1H); 4.95–5.03 (m, 1H); 4.62 (dd, J=9.9, 10.2, 1H); 4.20 (dd, J=8.1, 8.4, 1H); 3.75 (s, 3H). $^{13}C$ NMR ($^2HCCl_3$) Δ166.58, 165.33, 146.67, 131.75, 128.39, 127.12, 122.14, 71.72, 66.74, 51.68. IR (neat film, $cm^{-1}$) 1722.2, 1650.9, 1603.1, 1580.0, 1495.6, 1450.3, 1359.6, 1280.5, 1192.8, 1082.4, 1025.5, 974.4, 923.7, 864.9, 781.5, 756.0, 696.7. HRMS calcd for $C_{13}H_{13}NO_3$ 231.0895: Found $[M]^+$ 231.0888.

For the Z isomer, 5, colorless oil, $R_f$ 0.39, silica gel, 20:80 diethyl ether: petroleum ether, $[\alpha]^{20}_D$=−49.5°, c=0.094 in $CHCl_3$. $^1H$ NMR ($^2HCCl_3$) Δ7.96–7.99 (m, 2H); 7.48–7.52 (m, 1H); 7.40–7.46 (m, 2H); 6.44 (dd, J=7.2, 11.1, 1H); 5.92 (dd, J=11.4, 1.8, 1H); 5.71–5.80 (m, 1H); 4.87 (dd, J=9.9, 10.5, 1H); 4.10 (dd, J =8.4, 8.7, 1H); 3.76 (s, 3H). $^{13}C$ NMR ($^2HCCl_3$) Δ166.17, 165.29, 151.10, 131.50, 128.31, 127.52, 120.03, 73.38, 65.15, 51.44. IR (neat film, $cm^{-1}$) 1717.9, 1651.4, 1603.1, 1580.0, 1496.1, 1449.8, 1396.3, 1356.3, 1204.9, 1084.3, 1026.0, 965.2, 896.3, 819.6, 780.5, 696.2. HRMS calcd for $C_{13}H_{13}NO_3$ 231.0895: Found $[M]^+$ 231.0888.

Where R-(−)-methyl (E)-3-(4,5dihydro-2-phenyloxazolyl)-2-propenoate (ent4) and R-(+)-methyl (Z)-3-(4,5 dihydro-2-phenyl-4-oxazolyl)-2-propenoate (ent-5) are prepared from D-serine using the same methods as described above with respect to production of 4 and 5 from the L-isomer of serine, ent4 has $[\alpha]^{20}_D$=−51.5°, c=0.010 in $CHCl_3$. HRMS calculated for $C_{13}H_{13}NO_3$ 2231.0895: Found $[M]^+$ 231.0884. For ent-5, $[\alpha]^{20}_D$=+47.7°, c=0.013 in $CHCl_3$. HRMS calculated for $C_{13}H_{13}NO_3$ 2231.0895: Found $[M]^+$ 231.0894.

As shown in Scheme III, treatment of the (E)-isomer, 4, in aqueous acetone with a catalytic amount of osmium tetroxide and the N-oxide of N-methylmorpholine (NMO) at room temperature yields (71%) a mixture of the diol esters 6 (2R,3S,4S; $[\alpha]^{20}_D$ =−1.2°, c=0.006 in $CH_3OH$) and 7 (2S,3R,4S; $[\alpha]^{20}_D$=+73.9°, c=0.009 in $CH_3OH$) in a 1.6:1 ratio. The diasteromers are readily separated by column chromatography. This was performed with $R_4=CH_3$. Other selections for $R_4$ should be made carefully as they may affect the outcome of the reaction.

Scheme III

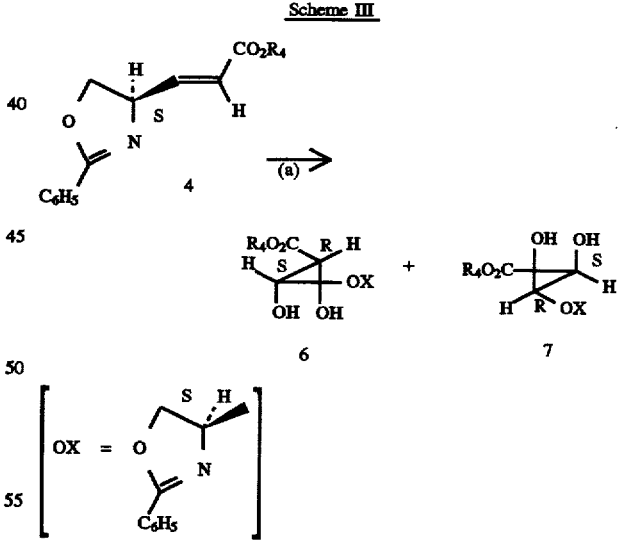

Several attempts to induce preferential formation of one of the diasteromers through stereoselective oxidation of 4 with the quinine derived, commercially available (DHQ)$_2$PHAL reagent in the presence of osmium tetroxide produced, in the best case, 65% of 6 and less than 5% of 7. Interestingly, results anticipated with the related (DHQD)$_2$PHAL reagent were not observed and improvement (both yield and stereochemical outcome) over NMO/$OsO_4$ was not achieved. Other conventional methods of hydroxylation may also be used to achieve the same result.

Where $R_4$ is $CH_3$, the hydroxylation reaction occurs as shown in Scheme IIIa:

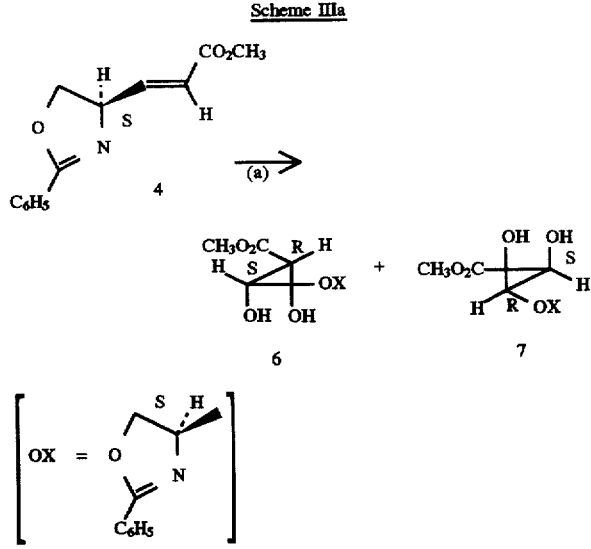

Experimentally, the E-alkene 4 (2.14 g, 9.3 mmol) in acetone (40 ml) and water (10 ml) was treated with N-methylmorpholine N-oxide (NMO) monohydrate (1.63 g, 12.0 mmol) and osmium tetroxide (1.0 ml of a 4% aqueous solution). Stirring was continued for 36 h at room temperature and the reaction was terminated by adding a saturated sodium bisulfite solution (5.0 ml) and stirring the resulting reaction mixture for an additional 30 min. The products were isolated by extracting the aqueous solution with an equal volume of ethyl acetate in three portions, combining the resulting solutions of organic solvents, drying them over sodium sulfate, filtering, and removing the solvent at reduced pressure.

The diols 6 and 7 were separated and purified by silica gel flash column chromatography (eluting with 98:2 $CH_3Cl:CH_3OH$).

Diol 6, mp 183° C., from ethanol, 1.06 g, 4 mmol, 43%, $[\alpha]^{20}_D=-1.2°$, c =0.006 in $CH_3OH$. $^1H$ NMR ($C^2H_3O^2H$): 7.91–7.95 (m, 2H), 7.50–7.56 (m, 1H), 7.14–7.47 (m, 2H), 4.44–4.63 (m, 4H), 4.00 (dd, J=5.7, 2.1, 1H), 3.76 (s, 3H); $^{13}C$ NMR ($C^2H_3O^2H$): 173.4, 165.7, 131.5, 128.1, 128.0, 127.1, 73.7, 72.1, 69.5, 67.8, 51.1; IR (KBr pellet, $cm^{-1}$) 3330.8, 1748.4, 1643.2, 1449.4, 1363.6, 1274.9, 1218.9, 1142.7, 1104.2, 736.8, 694.3; HRMS calculated for $[C_{13}H_{15}NO_5+H]$ 266.1028478: Found: $[M+H]^+$ 266.103644. Anal. Calculated for $C_{13}H_{15}NO_5$ C, 58.86 H, 5.70 N, 5.28. Found: C, 58.96 H, 5.87 N, 5.21.

Diol 7, mp 106° C., 668.5 mg, 2.5 mmol, 27%, $[\alpha]^{20}_D=+73.9°$, c=0.009 in $CH_3OH$. $^1H$ NMR ($C^2H_3O^2H$): 7.91–7.95 (m, 2H), 7.50–7.56 (m, 1H), 7.14–7.47 (m, 2H), 4.48–4.56 (m, 3H), 4.34 (d, J=3.0, 1H), 3.99 (dd, J=5.1, 3.0, 1H), 3.76 (s, 3H); $^{13}C$ NMR ($C^2H_3O^2H$): 173.1, 165.7, 131.5, 128.1, 128.0, 127.1, 73.1, 71.9, 69.3, 68.6, 51.2; IR (KBr pellet, $cm^{-1}$) 3356.9, 1732.9, 1656.8, 1449.4, 1359.7, 1244.0, 1139.8, 1093.6, 1045.3, 967.2, 808.1, 770.5, 694.3; HRMS calculated for $[C_{13}H_{15}NO_5+H]$ 266.1028478: Found: $[M+H]^+$ 266.103622. Anal. Calculated for $C_{13}H_{15}NO_5$ C, 58.86 H, 5.70 N, 5.28. Found: C, 58.86 H, 5.78 N, 5.07.

To determine the effect of other methods of dihydroxylation, the alkene 4 was treated with (DHQ)$_2$PHAL. The alkene 4 (216 mg, 0.94 mmol), (DHQ)$_2$PHAL (Aldrich, 7.3 mg, 9.4×10$^{-3}$ mmol), $K_3Fe(CN)_6$ (823 mg, 2.84 mmol), potassium carbonate (387.3 mg, 2.8 mmol) and methansulfonamide (89 mg, 0.94 mmol) were dissolved in t-butanol (5.0 ml) and water (5.0 ml) at room temperature with stirring. With stirring, osmium tetroxide (4% in water, 70 ml) was added and stirring was continued at room temperature for 48 h before saturated sodium bisulfite solution was added to quench the reaction. After stirring for an additional 20 min, the aqueous solution was extracted with three times its volume of ethyl acetate in three portions. The combined organic extracts were dried over sodium sulfate, filtered and the solvent evaporated. The diols 6 (166 mg, 0.63 mmol, 67%) and 7 (11 mg, 0.04 mmol, 4.5%) ratio 15:1 were separated and purified by silica gel flash column chromatography by elution with 98:2 $CHCl_3$ :$CH_3OH$.

When the diol 6 is treated with aqueous acid, hydrolysis of the oxazoline and recyclization to the 3,4-dihydroxy-5-hydroxymethylpyrrolidone benzoate ($R_4=CH_3$) ($[\alpha]^{20}_D=-47.6°$, c=0.006 in $CH_3OH$) (3R,4S,5S)-8 occurs in 61% yield. The structure of 8 is confirmed by x-ray crystallography. The diastereomer of 6, the diol 7, produces the corresponding ester ($[\alpha]^{20}_D=-110°$, c=0.006 in $CH_3OH$) (3S,4R,5S)-9 under the same conditions in 60% isolated yield. This reaction is shown in Scheme IV.

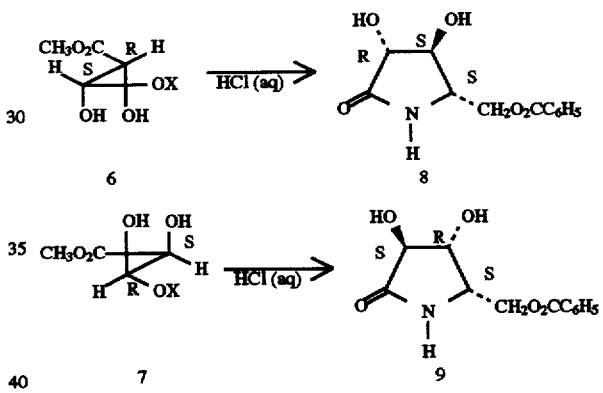

Experimentally, preparation of the lactam 8 from the diol 6 was as follows. With stirring, the diol 6 (2.646 g, 99.4 mmol) in THF (100 ml) was treated with aqueous hydrochloric acid solution (1.5M, 20 ml). After 24 hrs at room temperature, the reaction mixture was neutralized by addition of solid sodium bicarbonate, the solvent removed at reduced pressure, and the product isolated and purified from the residue by flash column chromatography over silica gel. The elution was begun with 10:90 $CH_3OH:CHCl_3$ mixture and this was followed by a mixture of 60:20:10:10 $CH_2Cl_2:CH_3CH_2OH:CH_3OH:NH_4OH$. Lactam 8, a white solid (1.5148 g, 60.4%, mp 138° C. was recrystallized in acetone/chloroform. Rf=0.17 in 10:90 $CH_3OH:CHCl_3$, $[\alpha]^{20}_D=-47.6°$ (c=0.006, methanol). $^1H$ NMR ($C^2H_3O^2H$): 8.04–8.08 (m, 2H), 7.58–7.63 (m, 1H), 7.44–7.49 (m, 2H), 4.60 (dd, J=11.7, 3.0, 1H), 4.32 (dd, J=12.0, 5.4, 1H), 4.17 (d, J=7.5, 1H), 4.05 (dd, J=7.2, 7.5, 1H), 3.63 (ddd, J=7.2, 5.4, 3.0, 1H); $^{13}C$ NMR ($C^2H_3O^2H$): 175.0, 166.3, 133.0, 129.5, 129.1, 128.2, 75.8, 75.5, 63.4, 56.3; IR (KBr pellet, $cm^{-1}$) 3369.4, 3289.4, 1672.1, 1600.8, 1453.8, 1384.8, 1323.1, 1280.6, 1129.2, 1102.2, 891.0, 707.8, 630.6; HRMS calcd for $[C_{12}H_{13}NO_5+H]$ 252.0871978: Found: $[M+H]^+$ 252.087132. Anal. Calcd for $C_{12}H_{13}NO_5$ C, 57.37 H, 5.22 N, 5.58. Found: C, 57.19 H, 5.43 N, 5.50.

Experimentally, preparation of the lactam 9 from the diol 7 was as follows. The diol 7 (95.2 mg, 0.36 mmol) was dissolved in methanol (3 ml) at room temperature and aqueous 1N HCl (1.0 ml) added. The resulting solution was permitted to stir at room temperature for 20 h and then neutralized by addition of solid sodium bicarbonate. The solvent was evaporated and the product was isolated and purified by flash column chromatography over silica gel, initially eluted with 10:90 $CH_3OH:CHCl_3$ and then a 60:20:10:10 mixture of $CH_2Cl_2:CH_3CH_2OH:CH_3OH:NH_4OH$. Lactam 9, a white solid (0.0598 g, 66.1%, mp 192° C., was recrystallized in ethanol, Rf=0.15 ($CH_3OH(10)/CHCl_3(90)$, $[\alpha]^{20}_D$=−110° (c=0.006, methanol). $^1H$ NMR ($C^2H_3O^2H$): 8.00–8.04 (m, 2H), 7.58–7.63 (m, 1H), 7.46–7.50 (m, 2H), 4.54 (dd, J=11.7, 3.3, 1H), 4.33 (dd, J=11.7, 4.8, 1H), 4.38 (dd, J=7.5, 8.1, 1H), 4.29 (d, J=8.1, 1H), 3.93 (ddd, J=7.5, 4.8, 3.3, 1H); $^{13}C$ NMR ($C_2H_3O^2H$): 175.0, 166.2, 133.0, 129.3, 129.0, 128.2, 74.5, 74.2, 63.0, 54.4; IR (KBr pellet, $cm^{-1}$) 3408.9, 3209.4, 1722.3, 1665.4, 1600.6, 1434.0, 1377.1, 1317.3, 1264.2, 1124.4, 1089.7, 1019.3, 920.0, 787.6, 707.8; HRMS calcd for $[C_{12}H_{13}NO_5+H]$ 252.0871978: Found: $[M+H]^+$ 252.087232. Anal. Calcd for $C_{12}H_{13}NO_5$ C, 57.37 H,5.22 N, 5.58. Found: C, 57.32 H, 5.30 N, 5.40

Then, the lactam-ester 8 with an excess of borane in tetrahydrofuran, cleanly undergoes reduction of both carbonyl functionalities simultaneously and quantitatively to yield the known L-iminoarabinitol [(2S,3S,4S)-3,4-dihydroxy-2-hydroxymethyl-pyrrolidine], 1, ($[\alpha]^{20}_D$=−11.9°, c=0.044 in $CH_3OH$; with the corresponding hydrochloride salt, $[\alpha]^{20}_D$= 28.8°, c=0.049 in $H_2O$; for the enantiomer $[\alpha]^{20}_D$=+7.8°, c=0.46 in $H_2O$ and for the enantiomeric hydrochloride salt, $[\alpha]^{20}_D$=+37.9°, c=0.53 in $H_2O$).

Experimentally, L-iminoarabinitol [(2S,3S,4S)-3,4-dihydroxy-2-hydroxymethyl-pyrrolidine] was produced from lactam 8 as follows. Lactam 8 (252 mg, 1.0 mmol) in THF (5.0 ml) at 0° C. was treated with borane in THF (1.0M, 15 ml, 15 mmol) and the reaction, under an atmosphere of argon, brought to reflux and heated, with stirring, overnight. The solvent was removed at reduced pressure and methanol added to destroy unreacted borane. The methanol solution was treated with aqueous hydrogen chloride (6N, 1 ml), slowly added dropwise and, at room temperature, the solution was stirred for an additional 30 min. Then, solid sodium hydroxide was added until the solution was basic and the product directly isolated (133 mg, 96% of theory) by aqueous solution ion-exchange chromatography on DOWEX 50WX8-100 and a final flash-chromatographic purification over a short silica gel column where it eluted with a 50:20:20:10 mixture of $CH_2Cl_2:CH_3CH_2OH:CH_3OH:NH_4OH$ to yield material with ($[\alpha]^{20}_D$=−11.9°, c=0.044 in $CH_3OH$; for the enantiomer $[\alpha]^{20}_D$=+7.8°, c=0.46 in $H_2O$). $^1H$ NMR ($C^2H_3O^2H$): 4.06 (ddd, J=5.7, 3.9, 3.9, 1H), 3.77 (dd, J=3.9, 3.9, 1H), 3.67 (dd, J=11.4, 4.8, 1H), 3.58 (dd, J=11.7, 6.6, 1H), 3.25 (s, N-H), 3.08 (dd, J=12.3, 5.7, 1H), 2.97 (ddd, J=6.6, 4.8, 3.9,1H), 2.80 (dd, J=12.3, 3.9, 1H); $^{13}C$ NMR ($C^2H_3O^2H$): 78.5, 77.0, 65.3, 61.5, 50.4; IR (neat film, $cm^{-1}$) 3423, 1645.2, 1530.4, 1422.4, 1206.4, 1115.7; HRMS calcd for $[C_5H_{11}NO_3+H]$ 134.0817184: Found: $[M+H]^+$ 134.081568: Found $[M+H]^+$ 134.081568. The hydrochloride, obtained on treatment of the free base with 6N HCl and recrystallized from methanol/acetone had $[\alpha]^{20}_D$=−28.8°, c=0.049 in $H_2O$ (lit for the enantiomeric hydrochloride salt, $[\alpha]^{20}_D$=+37.9°, c=0.53 in $H_2O$); $^1H$ NMR ($^2H_2O$): 4.26 (ddd, J=4.5, 3.3, 2.4, 1H), 4.02 (dd, J=3.6, 3.3, 1H), 3.88 (dd, J=12.0, 5.7, 1H), 3.76 (dd, J=12.3, 8.1, 1H), 3.55 (ddd, J=8.1, 5.7, 3.9, 1H), 3.51 (dd, J=12.6, 4.5, 1H), 3.29 (dd, J=12.6, 2.4, 1H); $^{13}C$ NMR ($^2H_2O$): 75.7, 74.3, 66.5, 58.9, 50.0; IR (KBr pellet, $cm^{-1}$) 3352, 1625.9, 1112.8, 1059.4, 1019.3.

A diasteromer of L-iminoarabinitol, the known L-iminoxylitol [(2S,3R,4R)-3,4-dihydroxy-2-hydroxymethylpyrrolidine], 1, ($[\alpha]^{20}_D$=−4.4°, c=0.010 in $CH_3OH$; for the corresponding hydrochloride salt, $[\alpha]^{20}_D$= −8.6°, c=0.010 in $H_2O$; lit $[\alpha]^{22}_D$=−1.3°, c=0.540 in $H_2O$) is obtained in 91% yield from 9 in the same way.

Experimentally, the following protocol was used. Lactam 9 (58.4 mg, 0.23 mmol) in THF (6.0 ml) at 0° C. was treated with borane in THF (1.0M, 3.5 ml, 3.5 mmol, 15 equiv.) and the reaction, under an atmosphere of argon, brought to reflux and heated, with stirring, for 5 hours. The solvent was removed at reduced pressure and methanol added to destroy unreacted borane. The methanol solution was treated with aqueous hydrogen chloride (6N, 1 ml), slowly added dropwise and, at room temperature, the solution was stirred for an additional 30 min. Then, solid sodium hydroxide was added until the solution was neutral and the product directly isolated (21.8 mg, 91% of theory) by ion-exchange chromatography on DOWEX 50WX8-100 and a final flash-chromatographic purification over a short silica gel column where it eluted with a 50:20:20:10 mixture of $CH_2Cl_2:CH_3CH_2OH:CH_3OH:NH_4OH$ to yield material with $[\alpha]^{20}_D$=−4.4°, c=0.010 in $CH_3OH$. $^1H$ NMR ($C^2H_3O^2H$): 4.13 (m, 1H), 4.07 (m, 1H), 3.75 (dd, J=11.4, 6.3, 1H), 3.63 (dd, J=11.4, 67.2, 1H), 3.35 (m, 1H), 3.28 (dd, J=12.9, 5.1, 1H), 2.78 (dd, J=12.9, 1.8, 1H); $^{13}C$ NMR ($C^2H_3O^2H$): 75.9, 75.6, 61.7, 58.8, 50.6; IR (neat film, $cm^{-1}$) 3380, 1654.8, 1420.5, 1048.2; HRMS calcd for $[C_5H_{11}NO_3+H]$ 134.0817184: Found: $[M+H]^+$ 134.081675. The hydrochloride, obtained on treatment of the free base with 6N HCl and recrystallized from methanol/acetone had $[\alpha]^{20}_D$=−8.6°, c=0.010 in $H_2O$; $^1H$ NMR ($^2H_2O$): 4.32 (d, br, J =3.3, 1H), 4.25 (s, br, 1H), 3.95 (dd, J=15.3, 8.7, 1H), 3.83 (m, 2H), 3.60 (dd, J=12.9, 4.2, 1H), 3.23 (d, br, J=12.9, 1H); $^{13}C$ NMR ($H_2O$): 74.3, 74.2, 63.0, 57.2, 50.5. IR (KBr pellet, $cm^{-1}$) 3383, 1625.9, 1412.8, 1308.6, 1101.3, 1047.3, 978.8, 913.2.

Both reactions are shown in Scheme V.

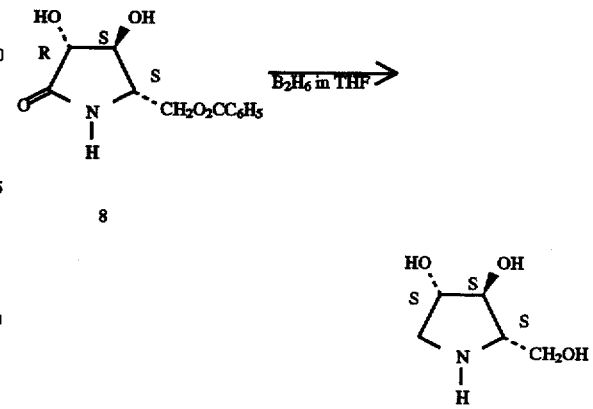

Scheme V

-continued
Scheme V

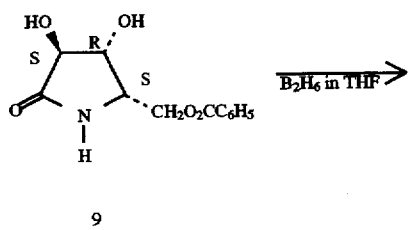

9

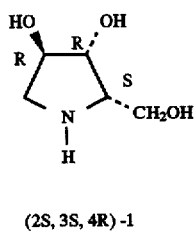

(2S, 3S, 4R)-1

In direct compliment to the above sequence of reactions, hydroxylation of the (Z)-isomer 5 (as by treatment of with osmium tetroxide) as shown in Scheme VI produces a mixture of the diol esters 11 (2R,3R,4S; $[\alpha]^{20}_D$=+48.3°, c=0.009 in $CH_3OH$) and 10 (2S,3S,4S; $[\alpha]^{20}_D$=+51.8°, c=0.007 in $CH_3OH$) in a 3.2:1 ratio (73% overall). As before, these isomers are readily separated by column chromatography.

Scheme VI

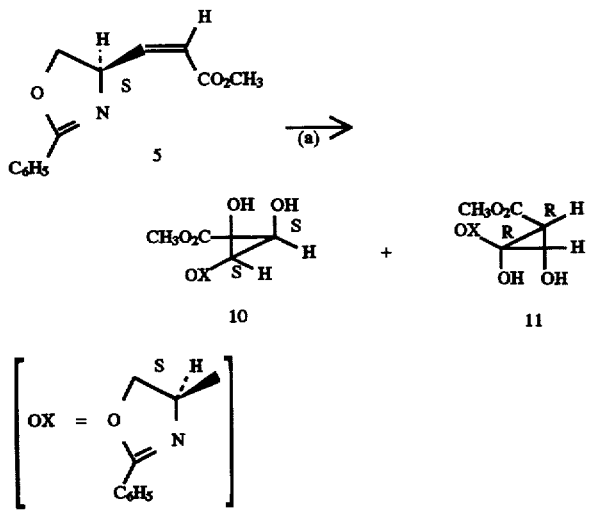

Experimental production of the diols 10 and 11 was as follows. The Z-alkene 5 (10.67 g, 46.2 mmol) in acetone (80 ml) and water (10 ml) was treated with N-methylmorpholine N-oxide (NMO) monohydrate (9.35 g, 69.2 mmol) and osmium tetroxide (6.8 ml of a 4% aqueous solution). Stirring was continued for 16 h at 0° C. and the reaction was terminated by adding a saturated sodium bisulfite solution (10.0 ml) and stirring the resulting reaction mixture for an additional 30 min. The products were isolated by extracting the aqueous solution with an equal volume of ethyl acetate in four portions, combining the resulting solutions of organic solvents, drying them over sodium sulfate, filtering, and removing the solvent at reduced pressure. Diols 10 and 11 were separated and purified by flash chromatography (eluting with 98.5:1.5 $CH_3Cl:CH_3OH$).

Diol 11, mp 159° C., 6.79 g, 25.6 mmol, 55.5%, $[\alpha]^{20}_D$= +48.3°, c=0.009 in $CH_3OH$. $^1H$ NMR ($C^2H_3O^2H$): 7.89–7.93 (m, 2H), 7.50–7.56 (m, 1H), 7.40–7.45 (m, 2H), 4.44–4.60 (m, 3H), 4.28 (d, J=4.8, 1H), 4.05 (dd, J=4.2, 4.2, 1H), 3.75 (s, 3H); $^{13}C$ NMR ($C^2H_3O^2H$): 172.9, 165.5, 131.4, 128.0, 127.9, 127.2, 73.7, 73.1, 68.6, 67.1, 51.0; IR (KBr pellet, $cm^{-1}$) 3444.6, 1736.8, 1644.2, 1450.4, 1370.3, 1296.0, 1238.2, 1109.0, 989.4, 949.9, 730.9, 694.3; HRMS calcd for [$C_{13}H_{15}NO_5$+H] 266.1028478: Found: [M+H]$^+$ 266.103391: Anal. Calcd for $C_{13}H_{15}NO_5$ C, 58.86 H, 5.70 N, 5.28. Found: C, 59.33 H, 5.86 N, 5.20.

Diol 10, mp 157° C., 2.15 g, 8.1 mmol 17.5%, $[\alpha]^{20}_D$= +51.8°, c=0.007 in $CH_3OH$. $^1H$ NMR ($C^2H_3O^2H$): 7.93–7.97 (m, 2H), 7.50–7.55 (m, 1H), 7.40–7.45 (m, 2H), 4.50–4.66 (m, 3H), 4.42 (dd, J=7.8, 7.8, 1H), 3.75 (s, 3H); $^{13}C$ NMR ($C^2H_3O^2H$): 173.8, 165.8, 131.3, 128.1, 128.0, 127.3, 73.0, 72.4, 69.2, 66.9, 51.0; IR (KBr pellet, $cm^{-1}$) 3393.5, 1710.7, 1640.4, 1449.4, 1373.2, 1238.2, 1063.6, 1034.7, 954.7, 687.5; HRMS calcd for [$C_{13}H_{15}NO_5$+H] 266.1028478: Found: [M+H]$^+$ 266.102911: Anal. Calcd for $C_{13}H_{15}NO_5$ C, 58.86 H, 5.70 N, 5.28. Found: C, 59.25 H, 5.80 N, 5.22.

Here too, several attempts to induce preferential formation of one of the diasteromers through stereoselective dihydroxylation met with limited success. The alkene 5 (290 mg, 1.25 mmol),(DHQD)$_2$PHAL (Aldrich, 9.8 mg, 12.5× $10^{-3}$ mmol), $K_3Fe(CN)_6$ (1.24 g, 3.77 mmol), potassium carbonate (520 mg, 3.8 mmol) and methansulfonamide (89 mg, 0.94 mmol) were dissolved in t-butanol (5.0 ml) and water (5.0 ml) at room temperature with stirring. With stirring, osmium tetroxide (4% in water, 74 ml) was added and stirring was continued at 0° C. for 18 h before saturated sodium bisulfite solution was added to quench the reaction. After stirring for an additional 20 min, the aqueous solution was extracted with three times its volume of ethyl acetate in three portions. The combined organic extracts were dried over sodium sulfate, filtered and the solvent evaporated. The diol 11 (281 mg, 1.06 mmol, 84.8%) was purified by silica gel flash column chromatography by elution with 98:2 $CHCl_3:CH_3OH$. Thus, treatment of 5 with (DHQD)$_2$PHAL yields 85% of the isomer 11. However, use of (DHQ)$_2$PHAL produced only 17% of 10 and 64% of 11.

As shown in Scheme VII, on treatment of the diol 10 with aqueous acid, hydrolysis and recyclization to the 3,4-dihydroxy-5-hydroxymethylpyrrolidone benzoate (3S,4S,5S)-12 occurs in 98% yield. Lactam 12 (3.16 g, 126 mmol, 98% of theory) was obtained from diol 10 (3.40 g, 128 mmol) by the same procedure used in the preparation of lactam 9 from diol 7 above. The product was recrystallized from methanol/diethyl ether with difficulty because of its limited solubility. Optical rotation was not taken because of its limited solubility.

For 12, mp 212° C., $^1H$ NMR ($C^2H_3O^2H$): 8.00–8.05 (m, 2H), 7.58–7.65 (m, 1H), 7.40–7.52 (m, 2H), 4.47 (dd, J=11.4, 4.5, 11H), 4.35 (dd, J=11.4, 5.1, 1H), 4.33 (d, J=5.7, 1H), 4.27 (dd, J=5.7, 1.5, 1H), 3.80 (ddd, J=5.1, 4.5, 1.5, 1H); $^{13}C$ NMR ($C^2H_3O_2H$): 176.5, 166.0, 133.0, 129.4, 129.1, 128.3, 70.0, 69.9, 64.2, 59.0; IR (KBr pellet, $cm^{-1}$) 3242.1, 1719.4, 1690.5, 1438.6, 1264.2, 1146.6, 1102.2, 767.6, 706.8; HRMS calcd for [$C_{12}H_{13}NO_5$+H] 252.0871978: Found: [M+H]$^+$ 252.087255: Anal. Calcd for $C_{12}H_{13}NO_5$ C, 57.37 H, 5.22 N, 5.58. Found: C, 57.07 H, 5.38 N, 5.59.

The diasteromeric diol 11 produces the corresponding ester ($[\alpha]^{20}_D$=−35.9°, c=0.005 in $CH_3OH$) (3R,4R,5S)-13 in 97% isolated yield under the same conditions.

Lactam 13, a white solid (20.0 mg, 0.08 mmol) was obtained from diol 11 (21.8 mg, 0.08 mmol, 98%) by the same procedure which was used in the preparation of lactam 9. It was recrystallized in acetone/hexanes. Rf=0.20 in 10:90

$CH_3OH:CHCl_3$. For 13, mp 145° C., $[\alpha]^{20}_D = -35.9°$ (c=0.005, methanol), $^1H$ NMR ($C^2H_3O^2H$): 8.06–8.09 (m, 2H), 7.58–7.63 (m, 1H), 7.45–7.51 (m, 2H), 4.60 (dd, J=11.4, 5.1, 1H), 4.43 (dd, J=5.4, 3.6, 1H), 4.40 (dd, J=11.1, 7.8, 1H), 4.27 (d, J=5.1, 1H), 3.95 (ddd, J=7.8, 5.1, 3.6, 1H); $^{13}C$ NMR ($C^2H_3O^2H$): 176.7, 166.4, 132.9, 129.7, 129.3, 128.1, 71.3, 69.1, 63.8, 54.4; IR (KBr pellet film, cm$^{-1}$) 3365.5, 1706.9, 1448.4, 1281.6, 1162.4, 1120.5, 712.5; HRMS calcd for $[C_{12}H_{13}NO_5+H]$ 252.0871978: Found: $[M+H]^+$ 252.087147; Anal. Calcd for $C_{12}H_{13}NO_5$ C, 57.37 H, 5.22 N, 5.58. Found: C, 56.31 H, 5.31 N. 5.38.

Scheme VII

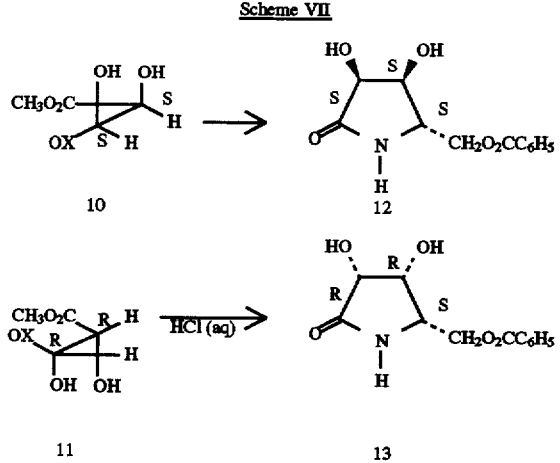

The reduction of the lactams 12 and 13 with removal of the benzoate is shown in Scheme VIII

Scheme VIII

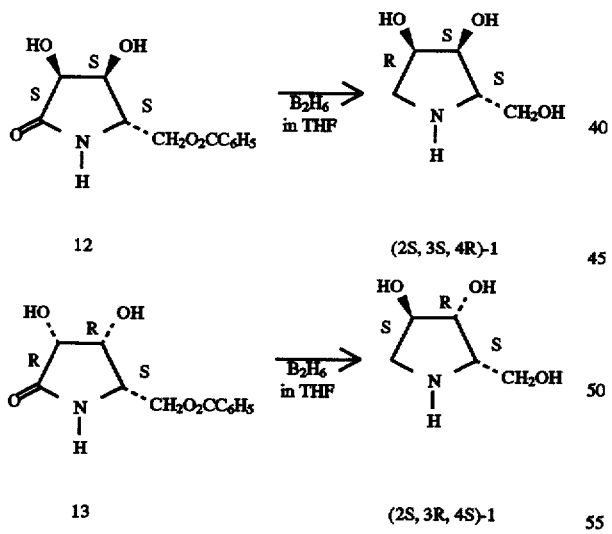

Reduction of the lactam 12 and removal of the benzoate is accomplished with borane in THF in 86% yield to produce L-iminoribitol [(2S,3S,4R)-3,4-dihydroxy-2-hydroxymethylpyrrolidine], 1, ($[\alpha]^{20}_D=-30.5$, c=0.039 in $CH_3OH$; and for the corresponding hydrochloride salt $[\alpha]^{20}_D=-62.3$, c=0.006 in $_2O$, lit=-59.0, c=0.59 in $H_2O$). L-iminoribitol was prepared as described above for L-iminoarabinatol and L-iminoxylitol (152 mg, 1.13 mmol, 86%) $[\alpha]^{20}_D=-30.5°$, c=0.039 in $CH_3OH$. $^1H$ NMR ($C^2H_3O^2H$): 4.06 (ddd, J=5.1, 5.1, 3.9, 1H), 3.79 (dd, J=6.9, 5.1, 1H), 3.66 (dd, J=11.7, 4.2, 1H), 3.54 (dd, J=11.7, 6.0, 1H), 3.26 (s, N-H), 3.09 (dd, J=12.3, 5.1, 1H), 3.00 (ddd, J=6.9, 6.0, 4.2, 1H), 2.75 (dd, J=12.3, 3.9, 1H); $^{13}C$ NMR ($C^2H_3O^2H$): 73.0, 71.1, 62.3, 61.8, 49.9; IR (neat film, cm$^{-1}$) 3380, 1651.9, 1532.3, 1426.2, 1346.2, 1103.2; HRMS calcd for $[C_5H_{11}NO_3+H]$ 134.0817184: Found: $[M+H]^+$ 134.081789.

The hydrochloride salt, obtained with 6N HCl in ethanol had $[\alpha]^{20}_D=-62.3°$, c=0.006 in $H_2O$. $^1H$ NMR ($^2H_2O$): 4.31 (ddd, J=3.9, 3.9, 1.8, 1H), 4.13 (dd, J=8.7, 3.9, 1H), 3.90 (dd, J=12.3, 3.3, 1H), 3.75 (dd, J=12.3, 6.0, 1H), 3.56 (ddd, J=8.7, 6.0, 3.3, 1H), 3.43 (dd, J=12.9, 3.9, 1H), 3.30 (dd, J=12.9, 1.8, 1H); $^{13}C$ NMR ($^2H_2O$): 71.1, 69.4, 61.7, 57.9, 49.5. IR (KBr pellet, cm$^{-1}$) 3395, 163.5, 1418.5, 1339.4, 1141.8, 106.1, 1043.4.

Its diasteromer, the known L-iminolyxitol [(2S,3R,4S)-3,4 dihydroxy-2-hydroxymethylpyrrolidine], 1, ($[\alpha]^{20}_D=-12.9°$, c=0.039 in $CH_3OH$; for the hydrochloride salt, $[\alpha]^{20}_D=-13.2$, c=0.014 in $H_2O$; lit $[\alpha]^{20}_D=17.2°$, c=0.4 in $H_2O$) is obtained in 96% yield from 13 with the same reagents. As described above for L-iminoarabinatol, L-iminoxylitol, and L-iminoribitol (24.9 mg, 0.18 mmol, 96%, $[\alpha]^{20}_D=-12.9°$, c=0.014 in $CH_3OH$. $^1H$ NMR ($C^2H_3O^2H$): 4.42 (ddd, J=7.5, 7.2, 3.9, 1H), 4.27 (dd, J=4.2, 3.9, 1H), 3.91(dd, J=12.0, 5.1, 1H), 3.81 (dd, J=12.0, 8.4, 1H), 3.66 (ddd, J=8.4, 5.1, 3.9, 1H), 3.45 (dd, J=12.0, 7.5, 1H), 3.12 (dd, J=12.0, 7.2, 1H); $^{13}C$ NMR ($C^2H_3O^2H$): 70.0, 69.8, 62.4, 57.7, 47.0; IR (neat film, cm$^{-1}$) 3318.3, 1770.5, 1634.5, 1418.5, 1133.1; HRMS calcd for $[C_5H_{11}NO_3+H]$ 134.0817184: Found: $[M+H]^+$ 134.081579) was obtained from the lactam 13 (48.9 mg, 0.194 mmol).

The hydrochloride obtained with 6N HCl in ethanol had $[\alpha]^{20}_D=-13.2°$, c =0.014 in $H_2O$. $^1H$ NMR ($^2H_2O$): 4.44 (ddd, J=8.2, 4.8, 3.9, 1H), 4.29 (dd, J=4.2, 3.9, 1H), 3.93 (dd, J=12.0, 4.8, 1H), 3.84 (dd, J=12.0, 8.2, 1H), 3.69 (ddd, J=8.2, 4.8, 4.2, 1H), 3.48 (dd, J=12.0, 7.5, 1H), 3.27 (s, N-H), 3.15 (dd, J=12.0, 7.5, 1H); $^{13}C$ NMR ($^2H_2O$): 70.0, 69.8, 62.5, 57.6, 47.0; IR (KBr pellet, cm$^{-1}$) 3423.4, 1612.4, 1406.9, 1341.4, 1137.9, 1101.2, 1041.5.

What is claimed:

1. A method of synthesizing an S-methyl-3-(4,5-dihydro-2-phenyl-4-oxazolyl)-2-propenoate comprising reacting a 4-(carbomethoxy)-2-phenyl-$\Delta^2$-oxazoline with diisobutyl aluminum hydride and a carboalkoxymethylene triphenylphosphorane of the following formula:

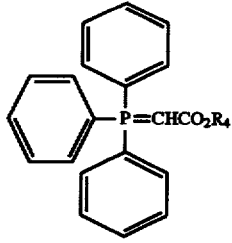

wherein $R_4$ is selected from the group consisting of $C_1$–$C_4$ alkyl groups.

2. The method of claim 1 wherein reacting the 4-(carbomethoxy)-2-phenyl-$\Delta^2$-oxazoline and diisobutyl aluminum hydride and a carboalkoxymethylene triphenylphosphorane of formula 3a comprises:

adding diisobutyl aluminum hydride to the 4-(carbomethoxy)-2-phenyl-$\Delta^2$-oxazoline to form an aldehyde;

quenching the aldehyde with an alcohol to form a mixture; and adding to the mixture a carboalkoxymethylene triphenylphosphorane of formula 3a.

3. The method of claim 2 wherein $R_4$ is methyl.

4. A method of synthesizing diol esters selected from the group consisting of the following formulas:

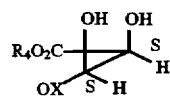 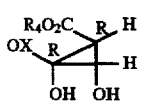 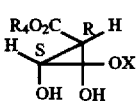 and 10  11  6

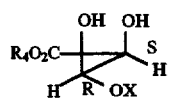

7 wherein OX is selected from the group consisting of

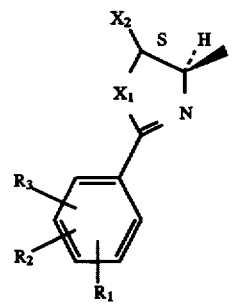 and 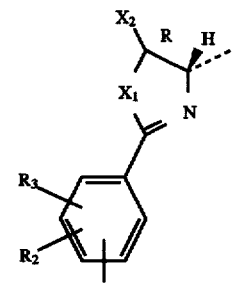, wherein $R_4$ is $CH_3$, $R_1$, $R_2$, and $R_3$ are each selected from the group consisting of H, $C_1$–$C_4$ alkyl and $C_1$–$C_4$ alkoxy, $X_2$ is H or $CH_3$ when $X_1$ is S, and $X_2$ is $CH_3$ when $X_1$ is O, comprising hydroxylating a methyl-3-(4,5-dihydro-2-phenyl-4-oxazolyl)-2-propenoate.

5. The method of claim 4 wherein hydroxylating the methyl-3-(4,5-dihydro-2-phenyl-4-oxazolyl)-2-propenoate comprises reacting the methyl-3-(4,5-dihydro-2-phenyl-4-oxazolyl)-2-propenoate and an N-oxide of N-methylmorpholine.

6. The method of claim 5 wherein reacting the methyl-3-(4,5-dihydro-2-phenyl-4-oxazolyl)-2-propenoate and the N-oxide of N-methylmorpholine comprises:

suspending the methyl-3-(4,5-dihydro-2-phenyl-4-oxazolyl)-2-propenoate in aqueous acetone; and adding osmium tetroxide and the N-oxide of N-methylmorpholine to the methyl-3-(4,5-dihydro-2-phenyl-4-oxazolyl)-2-propenoate.

7. A method of synthesizing a 3,4-dihydroxy-5-hydroxymethylpyrrolidone benzoate selected from the group consisting of the following formulas:

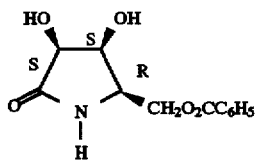

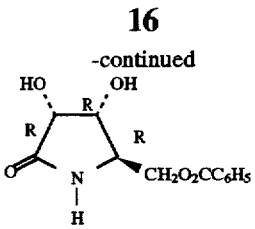

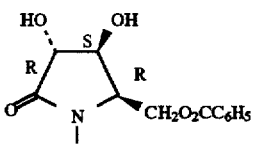 8

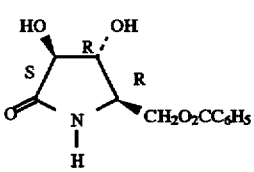 9

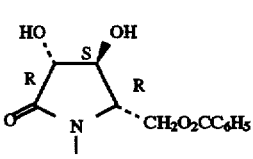 8

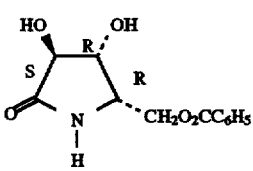 9

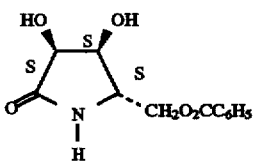 12

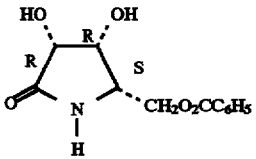 13 comprising reacting a diol ester selected from the group consisting of the following formulas:

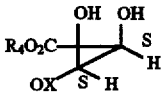 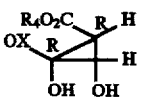 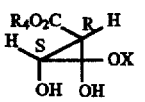

10  11  6

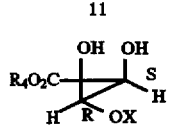

7 wherein OX is selected from the group consisting of

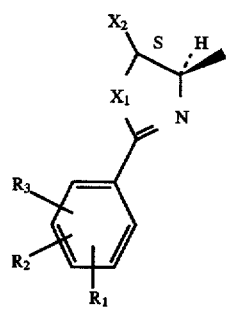 and 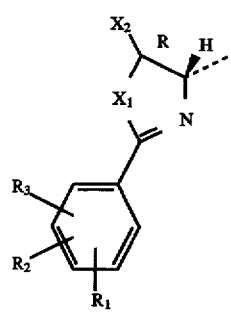

and wherein R₄ is CH₃,

R₁, R₂ and R₃ are each selected from the group consisting of H, $C_1$-$C_4$ alkyl and $C_1$-$C_4$ alkoxy, X₂ is H or CH₃ when X₁ is S, and X₂ is CH₃ when X₁ is O, with hydrochloric acid.

8. The method of claim 7 wherein reacting a diol ester selected from the group consisting of formulas 6, 7, 10 and 11 and hydrochloric acid comprises:

suspending the selected diol ester in tetrahydrofuran (THF) to form a mixture;

adding hydrochloric acid to the mixture; and adding sodium bicarbonate to the mixture to neutralize the mixture.

9. The method of claim 7 wherein reacting the diol ester selected from the group consisting of formulas 6, 7, 10 and 11 and hydrochloric acid comprises:

dissolving in methanol the diol ester selected from the group consisting of compounds of formulas 6, 7, 10 and 11 to form a mixture;

adding hydrochloric acid to the mixture; and adding sodium bicarbonate to the mixture to neutralize the mixture.

10. A method of synthesizing a 3,4-dihydroxy-2-hydroxymethylpyrrolidine comprising reacting a 3,4-dihydroxy-5-hydroxymethylpyrrolidone benzoate selected from the group consisting of the following formulas:

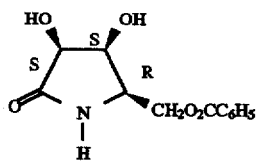

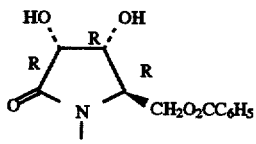

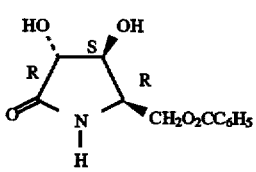

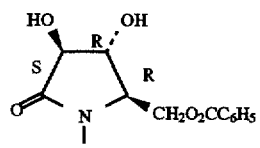

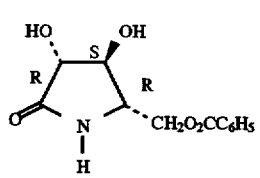

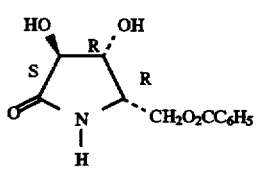

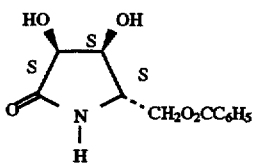

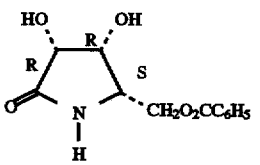

with borane in tetrahydrofuran.

11. A method of synthesizing a 3,4-dihydroxy-2-hydroxymethylpyrrolidine comprising:

reacting a methyl ester of formula 2 with a benziminoethyl ether of formula 2a:

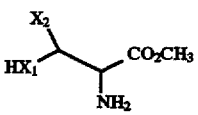 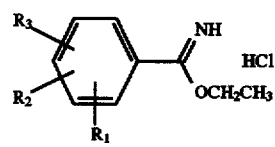

wherein X₁ is selected from the group consisting of O and S, X₂ is selected from the group consisting of H and CH₃ and R₁, R₂ and R₃ are selected from the group consisting of H, $C_1$-$C_4$ alkanes and $C_1$-$C_4$ ethers to form a 4-(carbomethoxy)-2-phenyl-$\Delta^2$-oxazoline;

reacting the 4-(carbomethoxy)-2-phenyl-$\Delta^2$-oxazoline with diisobutyl aluminum hydride and carboalkoxymethylene triphenylphosphorane of formula 3a:

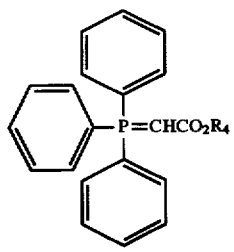

wherein $R_4$ is selected from the group consisting of $C_1-C_4$ alkanes;

to form an S-methyl-3-(4,5-dihydro-2-phenyl-4-oxazolyl)-2-propenoate;

reacting the S-methyl-3-(4,5-dihydro-2-phenyl-4-oxazolyl)-2-propenoate with an N-oxide of N-methylmorpholine to form diol esters selected from the group consisting of the following formulas:

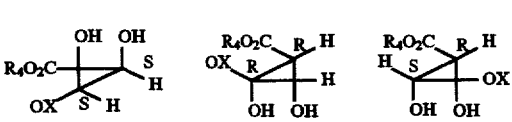

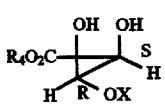

wherein OX is selected from the group consisting of

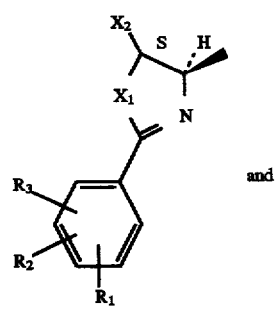 and 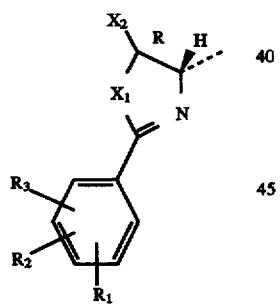

reacting the diol esters selected from the group consisting of formulas 6, 7, 10 and 11 with hydrochloric acid to form 3,4-dihydroxy-5-hydroxymethylpyrrolidone benzoate selected from the group consisting of the following formulas

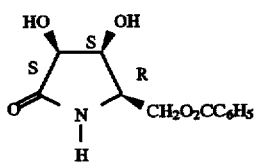

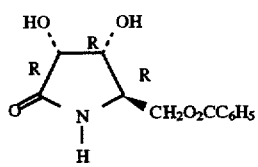

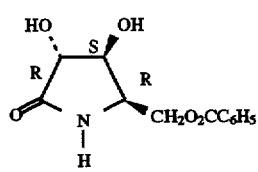

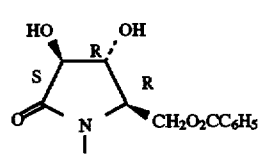

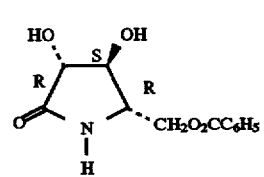

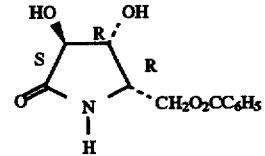

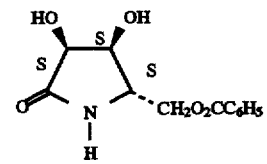

reacting the 3,4-dihydroxy-5-hydroxymethylpyrrolidone benzoate selected from the group consisting of compounds of formulas 8, 9, 12 and 13 with borane in tetrahydrofuran to form a 3,4-dihydroxy-2-hydroxymethyl-pyrrolidine.

12. The method of claim 11 wherein $X_1$ is O, $X_2$ is H, $R_1$, $R_2$ and $R_3$ are H and $R_4$ is methyl.

* * * * *

UNITED STATES PATENT AND TRADEMARK OFFICE
CERTIFICATE OF CORRECTION

PATENT NO. : 5,801,247
DATED : September 1, 1998
INVENTOR(S) : Dalton et al.

It is certified that error appears in the above-identified patent and that said Letters Patent is hereby corrected as shown below:

In column 16, the compound between lines 7-14, of the Letters Patent, delete "

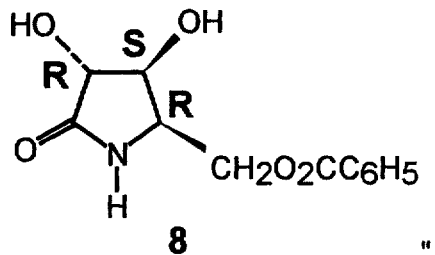

8

" and insert therefor--

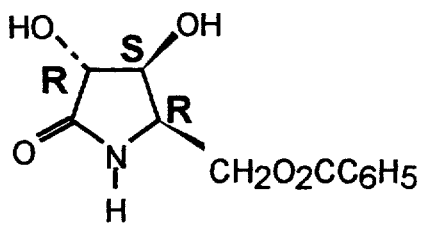

--.

UNITED STATES PATENT AND TRADEMARK OFFICE
CERTIFICATE OF CORRECTION

PATENT NO. : 5,801,247
DATED : September 1, 1998
INVENTOR(S) : Dalton et al.

Page 2 of 13

It is certified that error appears in the above-identified patent and that said Letters Patent is hereby corrected as shown below:

In column 16, the compound between lines 15-22, of the Letters Patent, delete

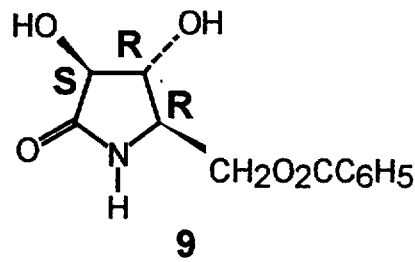

" 9 " and insert therefor--

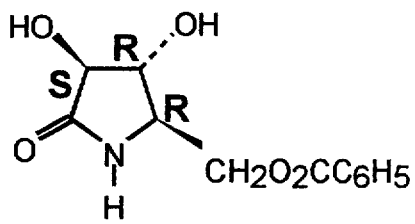

--.

UNITED STATES PATENT AND TRADEMARK OFFICE
CERTIFICATE OF CORRECTION

PATENT NO. : 5,801,247
DATED : September 1, 1998
INVENTOR(S) : Dalton et al.

It is certified that error appears in the above-identified patent and that said Letters Patent is hereby corrected as shown below:

In column 16, the compound between lines 23-27, of the Letters Patent, delete

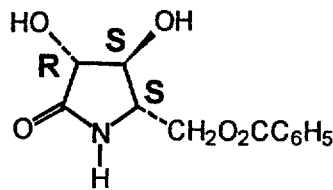

"         8         " and insert therefor--

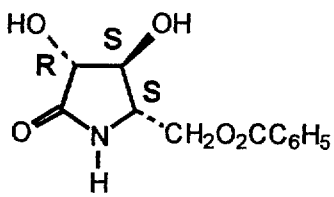

--.

In column 16, the compound between lines 28-35, of the Letters Patent, delete

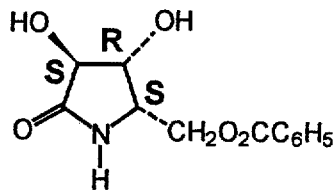

"         9         " and insert therefor--

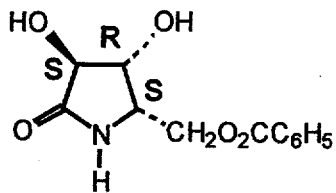

UNITED STATES PATENT AND TRADEMARK OFFICE
CERTIFICATE OF CORRECTION

PATENT NO. : 5,801,247  
DATED : September 1, 1998  
INVENTOR(S) : Dalton et al.

Page 4 of 13

It is certified that error appears in the above-identified patent and that said Letters Patent is hereby corrected as shown below:

In column 16, the compound between lines 36-43, of the Letters Patent, delete

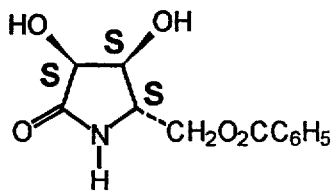

" 12 " and insert therefore--

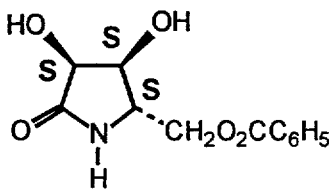

--.

UNITED STATES PATENT AND TRADEMARK OFFICE
CERTIFICATE OF CORRECTION

PATENT NO. : 5,801,247
DATED : September 1, 1998
INVENTOR(S) : Dalton et al.

It is certified that error appears in the above-identified patent and that said Letters Patent is hereby corrected as shown below:

In column 16, the compound between lines 44-49, of the Letters Patent, delete

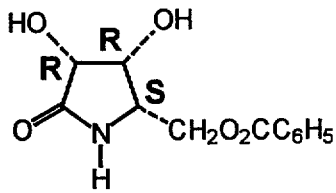

" 13 " and insert therefor--

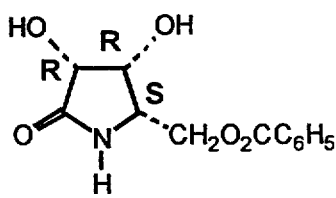

--.

UNITED STATES PATENT AND TRADEMARK OFFICE
CERTIFICATE OF CORRECTION

PATENT NO. : 5,801,247
DATED : September 1, 1998
INVENTOR(S) : Dalton et al.

It is certified that error appears in the above-identified patent and that said Letters Patent is hereby corrected as shown below:

In column 17, the compound between lines 57-63, of the Letters Patent, delete

" 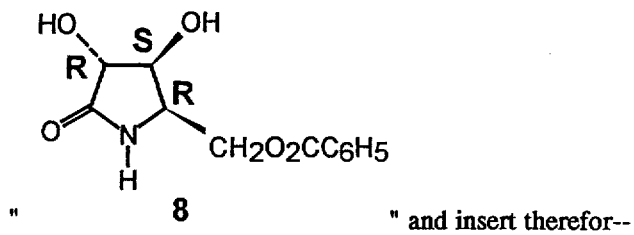 8 " and insert therefor--

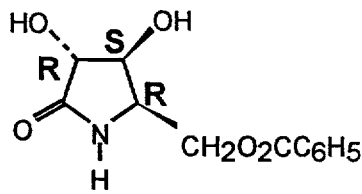

--.

UNITED STATES PATENT AND TRADEMARK OFFICE
CERTIFICATE OF CORRECTION

PATENT NO. : 5,801,247

DATED : September 1, 1998

INVENTOR(S) : Dalton et al.

Page 7 of 13

It is certified that error appears in the above-identified patent and that said Letters Patent is hereby corrected as shown below:

In column 18, the compound between lines 4-9, of the Letters Patent, delete

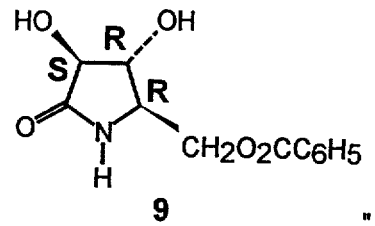

" 9 " and insert therefor --

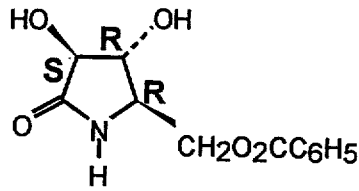

--.

UNITED STATES PATENT AND TRADEMARK OFFICE
CERTIFICATE OF CORRECTION

PATENT NO. : 5,801,247

DATED : September 1, 1998

INVENTOR(S) : Dalton et al.

Page 8 of 13

It is certified that error appears in the above-identified patent and that said Letters Patent is hereby corrected as shown below:

In column 18, the compound between lines 10-16, of the Letters Patent, delete

"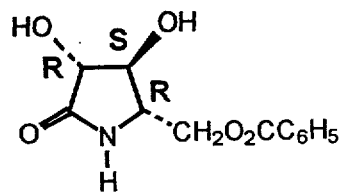
8
" and insert therefor--

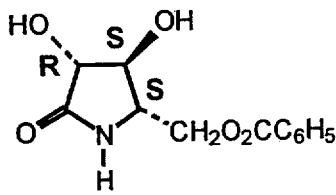

--.

UNITED STATES PATENT AND TRADEMARK OFFICE
CERTIFICATE OF CORRECTION

PATENT NO. : 5,801,247
DATED : September 1, 1998
INVENTOR(S) : Dalton et al.

It is certified that error appears in the above-identified patent and that said Letters Patent is hereby corrected as shown below:

In column 18, the compound between lines 17-23, of Letters Patent, delete

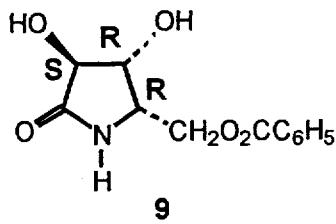

" 9 " and insert therefor --

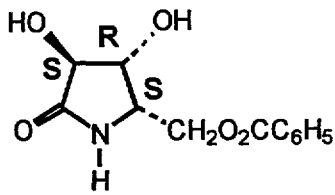

--.

UNITED STATES PATENT AND TRADEMARK OFFICE
CERTIFICATE OF CORRECTION

PATENT NO. : 5,801,247
DATED : September 1, 1998
INVENTOR(S) : Dalton et al.

It is certified that error appears in the above-identified patent and that said Letters Patent is hereby corrected as shown below:

In column 18, the compound between lines 24-31, of Letters Patent, delete

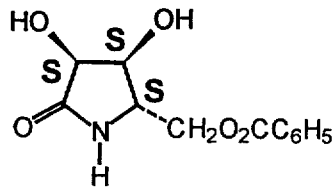

12

" and insert therefor --

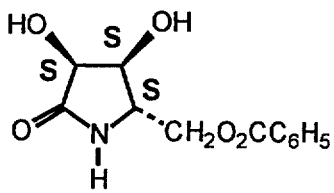

--.

UNITED STATES PATENT AND TRADEMARK OFFICE
CERTIFICATE OF CORRECTION

PATENT NO. : 5,801,247
DATED : September 1, 1998
INVENTOR(S) : Dalton et al.

Page 11 of 13

It is certified that error appears in the above-identified patent and that said Letters Patent is hereby corrected as shown below:

In column 18, the compound between lines 32-36, of Letters Patent, delete

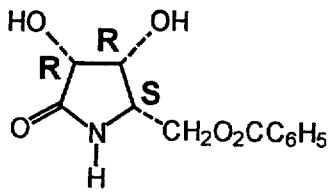

13

" and insert therefor --

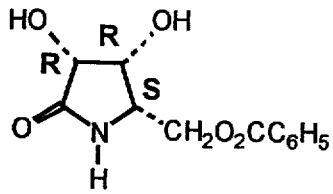

--.

UNITED STATES PATENT AND TRADEMARK OFFICE
CERTIFICATE OF CORRECTION

PATENT NO. : 5,801,247
DATED : September 1, 1998
INVENTOR(S) : Dalton et al.

Page 12 of 13

It is certified that error appears in the above-identified patent and that said Letters Patent is hereby corrected as shown below:

In column 20, the compound between lines 25-30, of Letters Patent, delete

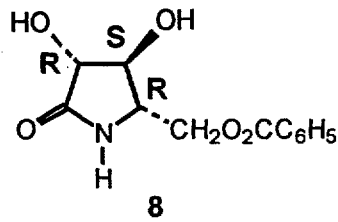

" 8 " and insert therefor --

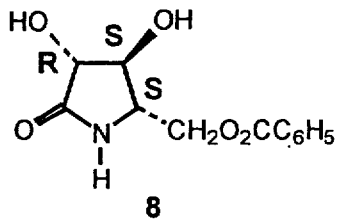

8 --.

UNITED STATES PATENT AND TRADEMARK OFFICE
CERTIFICATE OF CORRECTION

PATENT NO. : 5,801,247
DATED : September 1, 1998
INVENTOR(S) : Dalton et al.

It is certified that error appears in the above-identified patent and that said Letters Patent is hereby corrected as shown below:

In column 20, the compound between lines 31-36, of Letters Patent, delete

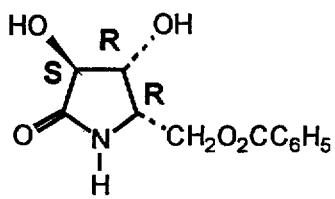

" 9 " and insert therefor --

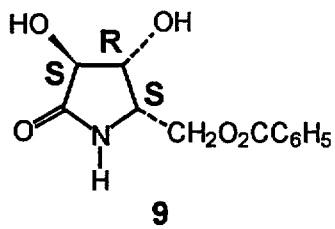

9 --.

Signed and Sealed this

Twenty-ninth Day of June, 1999

Attest:

Q. TODD DICKINSON

Attesting Officer     Acting Commissioner of Patents and Trademarks